United States Patent [19] [11] Patent Number: 6,034,119
Ono et al. [45] Date of Patent: Mar. 7, 2000

[54] AGENT FOR POTENTIATING NERVE GROWTH FACTOR ACTIVITY CONTAINING 1,2-ETHANEDIOL DERIVATIVE OR SALT THEREOF

[75] Inventors: Satoshi Ono; Mutsuko Maekawa; Kazunari Hirata; Hirokazu Narita, all of Toyama, Japan

[73] Assignee: Toyama Chemical Co., Ltd., Tokyo, Japan

[21] Appl. No.: 09/252,199

[22] Filed: Feb. 18, 1999

Related U.S. Application Data

[62] Division of application No. 09/001,656, Dec. 31, 1997, Pat. No. 5,922,721, which is a division of application No. 08/809,407, filed as application No. PCT/JP95/02162, Oct. 20, 1995, Pat. No. 5,807,887.

[30] Foreign Application Priority Data

Oct. 25, 1994 [JP] Japan ................................. 6-284272
Oct. 25, 1994 [JP] Japan ................................. 6-284273

[51] Int. Cl.[7] .................................................. A01N 43/32
[52] U.S. Cl. ........................ 514/433; 514/443; 514/469; 549/58; 549/469; 549/471
[58] Field of Search ........................... 549/58, 469, 471; 514/433, 443, 469

[56] References Cited

U.S. PATENT DOCUMENTS

| | | |
|---|---|---|
| 3,894,058 | 7/1975 | Effland et al. . |
| 5,254,595 | 10/1993 | Guzzi et al. . |
| 5,280,032 | 1/1994 | Ono et al. ................. 514/336 |
| 5,472,984 | 12/1995 | Ono et al. ................. 514/651 |
| 5,612,381 | 3/1997 | Ono et al. ................. 514/651 |
| 5,658,904 | 8/1997 | Ono et al. ................. 514/237.2 |
| 5,719,150 | 2/1998 | Ono et al. ................. 514/239.2 |
| 5,807,887 | 9/1998 | Ono et al. . |
| 5,872,117 | 2/1999 | Ono et al. . |

FOREIGN PATENT DOCUMENTS

| | | |
|---|---|---|
| 643634 | 11/1993 | Australia . |
| 383281 | 8/1990 | European Pat. Off. . |
| 4-95070 | 3/1992 | Japan . |
| 5-230103 | 9/1993 | Japan . |

OTHER PUBLICATIONS

Chemical Abstracts, vol. 119, No. 9, p. 72; col. 2; XP002048283; Aug. 30, 1993 S. Ono et al, "Protective Effect of R(–)–1–(Benzo[b]thiophen–5–yl)–2–[2–(N,N–diethylamino)ethoxyl] ethanol hydrochloride (T–588), a Novel Cerebral Activator, Against Experimental Cerebral Anoxia.".
Science,, vol. 259, No. 5093 (1993), pp. 373–377.
Biomedical. Letter, vol. 48, No. 191 (1993), pp. 209–227.

Primary Examiner—Mukund J. Shah
Assistant Examiner—Tamthom N. Truong
Attorney, Agent, or Firm—Oblon, Spivak, McClelland, Maier & Neustadt, P.C.

[57] ABSTRACT

A 1,2-ethanediol derivative represented by the general formula [I] or its salt:

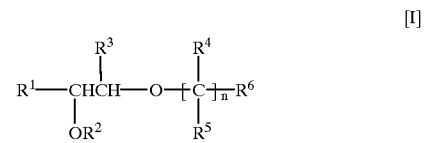

has a NGF activity-potentiating effect and is useful as a remedy for various diseases caused by degeneration of central nervous system or peripheral nervous system such as senile dementia of Alzheimer type, Huntington's chorea, various neuropathies, Riley-Day syndrome, traumatic nerve injury, amyotrophic lateral sclerosis (ALS) and the like.

5 Claims, No Drawings

AGENT FOR POTENTIATING NERVE GROWTH FACTOR ACTIVITY CONTAINING 1,2-ETHANEDIOL DERIVATIVE OR SALT THEREOF

This application is a Division of application Ser. No. 09/001,656 Filed on Dec. 31, 1997, now U.S. Pat. No. 5,922,721 allowed, which is a divisional of application Ser. No. 08/809,407, filed Apr. 23, 1997, now U.S. Pat. No. 5,807,887, which was filed as International Application No. PCT/JP95/02162 on Oct. 20, 1995.

TECHNICAL FIELD

This invention relates to a 1,2-ethanediol derivative or a salt thereof which potentiates the activity of a nerve growth factor (referred to hereinafter as NGF).

BACKGROUND ART

It has been known that NGF acts as a survival and maintenance as well as neurite outgrowth factor for sympathetic neurons and sensory neurons in the peripheral nervous system [Physiol. Rev., vol. 60, pages 1284–1335 (1980) and Ann. Rev. Biochem., vol. 51, pages 845–868 (1982)] and that high NGF levels were found in the regions innervated by the magnocellular neurons (hippocampus, neocortex, olfactory bulb), and in the regions containing the cell bodies of these neurons (septum, nucleus of the diagonal band of Broca, nucleus basalise of Meynert) and that NGF acts as neurotrophic factor for magnocellular cholinergic neurons [EMBO J., vol. 4, pages 1389–1393 (1985)].

NGF has also been drawing attention in terms of relation to central nervous diseases such as senile dementia of Alzheimer type [Science, vol. 232, page 1341 (1986)], Huntington's chorea [Neurosci. Lett., vol. 40, No. 2, pages 161–164 (1992)], and to peripheral nervous diseases such as various neuropathies {diabetic neuropathy [Brain Res., vol. 634, pages 7–12 (1994)], neuropathy caused by drugs (Brain Res., vol. 640, pages 195–204 (1994)] and the like}, Riley-Day syndrome [Japanese J. of Clinical Medicine, vol. 50, No. 4, pages 178–183 (1992)], traumatic neuropathy [Pharmacol. Ther., vol. 65, No. 1, pages 1–16 (1995)], amyotrophic lateral sclerosis (ALS) [Nature Medicine, vol. 1, No. 2, pages 168–172 (1995) and the like.

An attempt has been made to use NGF or a NGF-like substance for the treatment of central and peripheral nervous diseases described above [Brain and Nerve, vol. 43, No. 12, pages 1101–1112 (1991) and the like]. However, these substances are all proteins, and when they are used as drugs, their stability, antigenicity and the like will become a problem. Therefore, a compound useful as a drug for potentiating the NGF activity has been desired.

DISCLOSURE OF THE INVENTION

Under such circumstances, the present inventors have made extensive research and have consequently found that a 1,2-ethanediol derivative represented by the following general formula [I] or a salt thereof potentiates the NGF activity:

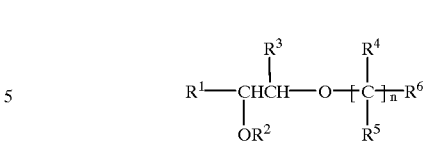

[I]

wherein $R^1$ represents a substituted or unsubstituted henyl, naphthyl, indanyl, indenyl, tetrahydronaphthyl or eterocyclic group; $R^2$ represents a hydrogen atom, a lower alkyl group or a hydroxyl-protecting group; $R^3$ represents a hydrogen atom or a lower alkyl group; $nR^4$'s may be the same as or different from one another and each represents a hydrogen atom or a lower alkyl group; $nR^5$'s may be the same as or different from one another and each represents a hydrogen atom or a lower alkyl group; $R^6$ represents a substituted or unsubstituted amino or nitrogen-containing heterocyclic group or an ammonio group; and n represents 0 or an integer of 1 to 6.

This invention is explained in detail below.

In the present specification, unless otherwise specified, the terms used herein have the following meanings.

The term "halogen atom" means fluorine atom, chlorine atom, bromine atom or iodine atom. The term "lower alkyl group" means a $C_{1-6}$ alkyl group such as methyl, ethyl, n-propyl, isopropyl, n-butyl, isobutyl, tert-butyl, pentyl, hexyl or the like. The term "lower alkenyl group" means a $C_{1-6}$ alkenyl group such as vinyl, propenyl, butenyl, pentenyl, hexenyl or the like. The term "lower alkenyloxy group" means a $C_{1-6}$ alkenyl-O— group. The term "cycloalkyl group" means a $C_{3-6}$ cycloalkyl group such as cyclopropyl, cyclobutyl, cyclopentyl, cyclohexyl or the like. The term "lower alkoxy group" means a $C_{1-6}$ alkyl-O— group. The term "lower alkylthio group" means a $C_{1-6}$ alkyl-S— group. The term "halo-lower alkyl group" means a halogen-$C_{1-6}$ alkyl group. The term "aryl group" means a phenyl, naphthyl, indanyl or indenyl group. The term "aryloxy group" means an aryl-O— group. The term "ar-lower alkyl group" means an ar-$C_{1-4}$ alkyl group such as benzyl, diphenylmethyl, trityl, phenethyl or the like. The term "ar-lower alkoxy group" means an ar-$C_{1-4}$ alkyl-O— group. The term "ar-lower alkylthio group" means an ar-$C_{1-4}$ alkyl-S— group. The term "ar-lower alkenyl group" means an ar-$C_{2-4}$ alkenyl group. The term "lower alkylenedioxy group" means a $C_{1-4}$ alkylenedioxy group such as methylenedioxy, ethylenedioxy or the like. The term "lower acyl group" means a $C_{1-6}$ acyl group such as formyl, acetyl, butyryl or the like. The term "aroyl group" means an aryl-CO— group. The term "lower alkyl-sulfonyl group" means a $C_{1-6}$ alkyl-$SO_2$ group. The term "ar-lower alkylsulfonyl group" means an ar-$C_{1-6}$ alkyl-$SO_2$-group. The term "arylsulfonyl group" means an aryl-$SO_2$-group. The term "arylsulfonylamino group" means an aryl-$SO_2NH_2$— group. The term "lower alkylsulfonylamino group" means a $C_{1-6}$ alkyl-$SO_2NH$— group. The term "di-lower alkyl amino group" means a $(C_{1-6}alkyl)_2N$— group such as dimethylamino, diethylamino or the like. The term "ammonio group" means a tri-lower alkylammonio group such as trimethylammonio, triethylammonio or the like. The term "nitrogen-containing heterocyclic group" means a heterocyclic group of a 5-membered or 6-membered ring, fused ring or bridged ring containing at least one nitrogen atom as hetero atom forming the ring which may further contain at least one oxygen or sulfur atom such as pyrrolyl, pyrrolidinyl, piperidyl, piperazinyl, imidazolyl, pyrazolyl, pyridyl, tetrahydropyridyl, pyrimidinyl, morpholinyl, thiomorpholinyl, quinolyl, quinolidinyl, tetrahydroquinolinyl, tetrahydroisoquinolinyl, quinuclidinyl, thiazolyl, tetrazolyl, thiadiazolyl, pyrrolinyl, imidazolinyl, imidazolidinyl, pyrazolinyl, pyrazolidinyl, purinyl, indazolyl or the like. The term "heterocyclic group" means the above-mentioned nitrogen-containing heterocyclic group or a 5-membered or 6-membered ring, a fused ring or a bridged ring containing at least one hetero atom selected from the group consisting of nitrogen, oxygen or sulfur atom which may contain at least one oxygen or sulfur atom as hetero atom forming the ring such as furyl, thienyl, benzothienyl, pyranyl, isobenzofuranyl, oxazolyl, benzofuranyl, indolyl, benzimidazolyl, benzoxazolyl, benzothiazolyl, quinoxalyl, dihydroquinoxalinyl, 2,3-dihydrobenzothienyl, 2,3-dihydrobenzopyrrolyl, 2,3-dihydro-4H-1-thianaphthyl, 2,3-dihydrobenzofuranyl, benzo[b]dioxanyl, imidazo[2,3-a]pyridyl, benzo[b]piperazinyl, chromenyl, isothiazolyl, isoxazolyl, thiadiazolyl, oxadiazolyl, pyridazinyl, isoindolyl, isoquinoiyl or the like. The term "heterocyclic carbonyl group" means a heterocyclic-CO— group.

The substituents of the phenyl, naphthyl, indanyl, indenyl, tetrahydronaphthyl and heterocyclic groups in $R^1$ include, Lor example, halogen atoms; substituted or unsubstituted amino, lower alkyl, aryl, ar-lower alkyl, lower alkoxy, ar-lower alkoxy, aryloxy, carbamoyloxy, lower alkylthio, lower alkenyl, lower alkenyloxy, ar-lower alkylthio, ar-lower alkylsulfonyl, arylsulfonyl, lower alkylsulfonylmaino, arylsulfonylamino and heterocyclic groups; protected amino groups; protected or unprotected hydroxyl groups; nitro group; oxo group; lower alkylenedioxy groups and the like.

The substituents of the lower alkyl, aryl, ar-lower alkyl, lower alkoxy, ar-lower alkoxy, aryloxy, carbamoyloxy, lower alkylthio, lower alkenyl, lower alkenyloxy, ar-lower alkylthio, ar-lower alkylsulfonyl, arylsulfonyl, lower alkylsulfonylmaino, arylsulfonylamino and heterocyclic groups in the substituent of the phenyl, naphthyl, indanyl, indenyl, tetrahydronaphthyl and heterocyclic groups of $R^1$; and the substituents of the nitrogen-containing heterocyclic group in $R^6$ include halogen atoms, protected or unprotected hydroxyl groups, protected or unprotected carboxyl groups, protected or unprotected amino groups, lower alkyl groups which is unsubstituted or substituted by a protected or unprotected hydroxyl group, halogen-substituted or unsubstituted aryl groups, halogen-substituted or unsubstituted aroyl groups, lower alkoxy group-substituted or unsubstituted lower alkoxy groups, halo-lower alkyl groups, lower acyl groups, ar-lower alkyl groups, ar-lower alkenyl groups, heterocyclic groups, heterocyclic carbonyl groups, oxo group, lower alkylsulfonyl groups and arylsulfonyl groups and these may be substituted by at least one of these substituents.

The substituents of the amino group in $R^1$ and the substituted amino group in $R^6$ include protected or unprotected hydroxyl groups, lower alkyl groups which are unsubstituted or substituted by a protected or unprotected hydroxyl or carboxyl group, cycloalkyl groups, aryl groups, lower acyl groups, ar-lower alkyl groups, heterocyclic groups, oxo group-substituted or unsubstituted heterocyclic carbonyl groups, adamantyl group, lower alkylsulfonyl groups and arylsulfonyl groups, and these may be substituted by at least one of these substituents.

Hydroxyl-protecting group of $R^2$ and the protective group of hydroxyl, carboxyl and amino groups included in the substituents include usual hydroxyl-, carboxyl- and amino-protecting groups mentioned in "Protective Groups in Organic Synthesis" by Theodra W. Greene (1981), published by John Wiley & Sons, Inc. and in particular, as the hydroxyl-protecting group, there are mentioned lower alkyl groups, lower acyl groups, tetrahydropyranyl group and substituted or unsubstituted ar-lower alkyl groups such as benzyl.

The salt of the 1,2-ethanediol derivative represented by the general formula [I] may be any pharmaceutically acceptable salt and includes salts with mineral acids such as hydrochloric acid, hydrobromic acid, sulfuric acid, phosphoric acid and the like; salts with carboxylic acids such as formic acid, acetic acid, oxalic acid, fumaric acid, maleic acid, malic acid, tartaric acid, aspartic acid and the like; salts with sulfonic acids, such as methanesulfonic acid, benzenesulfonic acid, p-toluenesulfonic acid, naphthalenesulfonic acid and the like; salts with alkali metals such as sodium, potassium and the like; etc.

When the 1,2-ethanediol derivative represented by the general formula [I] or its salt has isomers (for example, optical isomers, geometrical isomers, tautomers and the like), this invention includes all these isomers, and also include hydrates, solvates and all crystal forms of the above compound or its salt.

The 1,2-ethanediol derivative represented by the general formula [I] or its salt can be formed into a preparation such as tablet, capsule, powder, granules, fine granules, pill, suspension, emulsion, solution, syrup, injection or the like using a pharmaceutically acceptable preparation adjuvant such as excipient, carrier, diluent or the like in a conventional manner, and the resulting preparation can be administered orally or parenterally. The administration route, dosage and number of administrations may be adequately varied depending upon the age, weight and symptom of a patient and in the case of oral administration, the dosage is usually 0.01 to 500 mg/day per adult and this may be administered in one to several portions.

An explanation is made below of a process for producing the 1,2-ethanediol derivative represented by the general formula [I] or its salt.

The 1,2-ethandiol derivative represented by the general formula [I] or its salt can be produced by the methods described in JP-A-3-47,158; JP-A-3-197,422; JP-A-3-232,830; and JP-A-4-95,070 and the like or methods known per se or in appropriate combinations thereof, for example, according to each of the following production processes.

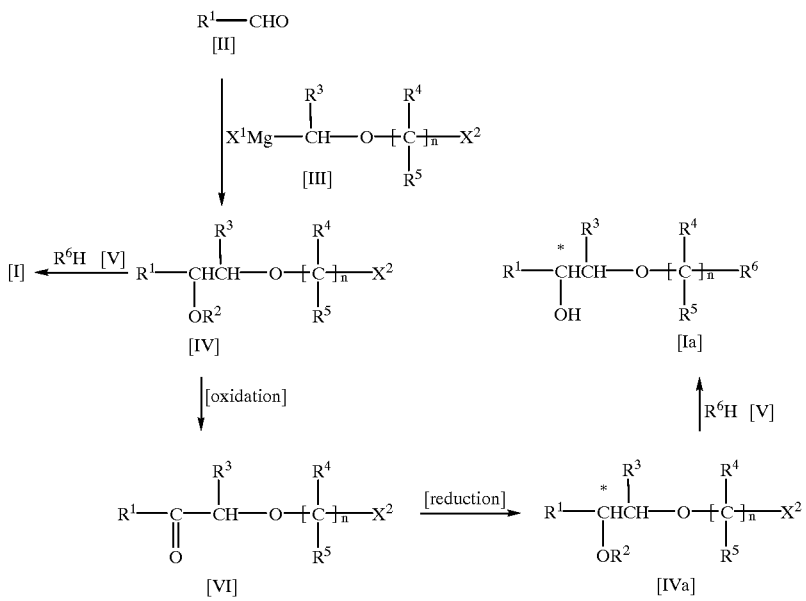

wherein $R^1$, $R^2$, $R^3$, $R^4$, $R^5$, $R^6$ and n have the same meanings as described above, * represents an asymmetric carbon and $X^1$ and $X^2$ represent halogen atoms.

PRODUCTION PROCESS 1

(1) A compound of the general formula [IV] or its salt can be produced by reacting a compound of the general formula [II] with a compound of the general formula [III].

In this reaction, any solvent may be used as far as it does not adversely affect the reaction, and the solvent includes ethers such as diethyl ether, tietrahydrofuran, dioxane and the like; aromatic hydrocarbons such as benzene, toluene and the like; etc. These solvents may be used alone or in admixture of two or more.

In the above reaction, the amount of the compound of the general formula [III] used is 0.8 to 100 moles, preferably 0.8 to 10 moles, per mole of the compound of the general formula [II].

Said reaction may be carried out usually at a temperature of −78° C. to +100° C., preferably −78° C. to +50° C., for a period of 5 minutes to 24 hours.

The compound of the general formula [IV] or its salt thus obtained may be used in the subsequent reaction as it is without being isolated.

Incidentally, the compound of the general formula [III] used here can be produced by a method known per se, for example, the method described in Bull. Soc. Chim. Fr., 1967(5), pages 1533–1540.

(2) The compound of the general formula [I] or its salt can be produced by reacting the compound of the general formula [IV] or its salt with a compound of the general formula [V] or its salt in the presence or absence of a catalyst and in the presence or absence of a base.

In this reaction, any solvent may be used as far as it does not adversely affect the reaction, and the solvent includes halogenated hydrocarbons such as methylene chloride, zhloroform and the like; ethers such as tetrahydrofuran, dioxane and the like; alcohols such as ethanol, propanol, butanol and the like; nitriles such as acetonitrile and the like; amides such as N,N-dimethylformamide and the like; water; etc. These solvents may be used alone or in admixture of two or more.

The optionally used catalyst includes, for example, potassium iodide, sodium iodide and the like.

The amount of the catalyst used is 0.1 to 1 mole per mole of the compound of the general formula [IV] or its salt.

The optionally used base includes organic and inorganic bases such as triethylamine, diisopropylethylamine, 1,8-diazobicyclo[5.4.0]undec-7-ene (DBU), pyridine, potassium tert-butoxide, sodium carbonate, potassium carbonate, sodium hydride and the like. Also, the compound of the general formula [V] or its salt can be used as the base.

The amount of the compound of the general formula [V] or its salt or the base used is at least one mole, preferably 1 to 20 moles, per mole of the compound of the general formula [IV] or its salt.

Said reaction may be carried out usually at a temperature of 10° C. to 150° C., preferably 20° C. to 100° C., for a period of 10 minutes to 20 hours.

The compounds or bases used in each of the above production processes can also be used as solvents depending upon their properties.

When the compounds of the general formulas [II], [III], [IV] and [V] in the above-mentioned production processes have isomers (for example, optical isomers, geometrical isomers, tautomers and the like), all of them can be used, and also, they can be used in the form of hydrates and solvates and in all crystal forms.

When the compounds of the general formulas [II], [III], [IV] and [V] have a hydroxyl group, an amino group or a carboxyl group, said hydroxyl, amino or carboxyl group may previously be protected with a conventional protective group and, after the reaction, the protective group can, if necessary, be removed in a manner known per se.

PRODUCTION PROCESS 2

(1) A compound represented by the general formula [VI] or its salt can be produced by oxidizing the compound represented by the general formula [IV] or its salt by a conventional method as described in "Modern Synthetic Reactions", Second Edition by Herbert O. House (1972) published by W.A. Benjamin, Inc., or the like.

Any solvent may be used in this reaction as far as it does not adversely affect the reaction, and the solvent includes ethers such as diethyl ether, tetrahydrofuran, dioxane and the like; aromatic hydrocarbons such as benzene, toluene and the like; etc. These solvents may be used alone or in admixture of two or more.

The compound represented by the general formula [VI] or its salt thus obtained can be used in the subsequent reaction as it is without being isolated.

(2) A compound represented by the general formula [IVa] or its salt can be produced by reducing the compound represented by the general formula [VI] or its salt in the presence or absence of a catalyst and in the presence or absence of a base by a method known per se, for example, the method described in Tetrahedron Letters, vol. 33, No. 29, page 4102, or the like.

(3) The compound of the general formula [I] or its salt can be produced by reacting the compound represented by the general formula [IVa] or its salt with the compound represented by the general formula [V] in the presence or absence of a catalyst and in the presence or absence of a base in the same manner as in the Production Process 1 (2) mentioned above.

The 1,2-ethanediol derivative represented by the general formula [I] or its salt thus obtained can be purified and isolated by a conventional method such as extraction, crystallization, distillation, column chromatography or the like. Also, the 1,2-ethanediol derivative represented by the general formula [I] or its salt can be converted to another 1,2-ethanediol derivative or its salt by an adequate combination of known methods per se such as oxidation reaction, reduction reaction, addition reaction, acylation reaction, alkylation reaction, sulfonylation reaction, deacylation reaction, substitution reaction, dehydration reaction, hydrolysis reaction and the like.

Reference Examples and Production Examples are shown below for more specifically explaining the processes for producing the compounds of this invention.

In the following Reference Examples and Production Examples, the mixing ratio of the solvents is all indicated in volume basis. In column chromatographic purification, Silica gel (70–230 meshes, mfd. by Merck & Co., Inc.) is used as a support. In moderate pressure column chromatographic purification, LC Sorb SP-A-Si (mfd. by Chemco) are used as a support.

The compound of the general formula [II], a starting material for producing the compound of the present invention, is known per se. Otherwise, it can be prepared by a method known per se or an adequate combination of methods known per se in accordance with the following Reference Examples.

REFERENCE EXAMPLE 1

(1) In 250 ml of water is suspended 25.0 g of 3-fluoro-4-methylaniline, and 34.7 ml of conc. hydrochloric acid is added to the suspension. Thereafter, the resulting mixture is cooled to 5° C. To this mixture is dropwise added a solution of 15.2 g of sodium nitrite in 20 ml of water at a temperature of 5° C. to 10° C. over one hour. The reaction mixture thus obtained is dropwise added to a solution of 64.0 g of potassium O-ethyl dithiocarbonate in 200 ml of water at a temperature of 50° C. to 60° C. over one hour. The resulting reaction mixture is cooled to room temperature, and thereafter, 300 ml of ethyl acetate is added thereto. Thereafter, the resulting organic layer is separated, washed with a saturated saline solution and then dried over anhydrous magnesium sulfate. Then, the solvent is removed by distillation under reduced pressure, to obtain brown, oily O-ethyl S-(3-fluoro-4-methyl)phenyl dithiocarbonate.

(2) To a solution of O-ethyl S-(3-fluoro-4-methyl) phenyl dithiocarbonate in 150 ml of methanol is added 22.4 g of potassium hydroxide at room temperature under a nitrogen atmosphere. The resulting mixture is stirred at room temperature for five hours. Thereafter, 34.8 ml of bromoacetaldehyde diethyl acetal is added to the thus stirred mixture. The resulting mixture is refluxed for six hours and then cooled. Thereafter, insolubles are removed from the thus cooled mixture by filtration. The resulting filtrate is concentrated under reduced pressure. To the residue obtained are added 300 ml of water and 150 ml of ethyl acetate, and the resulting organic layer is separated, washed with a saturated saline solution and dried over anhydrous magnesium sulfate. Thereafter, the solvent is removed from the thus dried layer by distillation under reduced pressure. The residue thus obtained is purified by a column chromatography [eluent:hexane:ethyl acetate=10:1], to obtain 43.6 g of oily 1,1-diethoxy-2-(3fluoro-4-methylphenylthio)ethane.

NMR (CDCl$_3$) δ value: 1.19 (6H, t, J=7.0 Hz), 2.22 (3H, d, J=2.0 Hz), 3.09 (2H, d, J=5.4 Hz), 3.58 (2H, q, J=7.0 Hz), 3.63 (2H, q, J=7.0 Hz), 4.63 (1H, t, J=5.4 Hz), 6.9–7.3 (3H, m)

(3) To a solution of 43.6 g of 1,1-diethoxy-2-(3-fluoro-4-methylphenylthio)ethane in 400 ml of toluene is added 80 ml of 85% phosphoric acid. The resulting solution is refluxed for 2.5 hours using an azeotropic dehydration apparatus. After cooling, to the thus cooled reaction mixture are added 600 ml of water and 200 ml of ethyl acetate, and the resulting organic layer is separated, washed successively with water and a saturated saline solution and then dried over anhydrous magnesium sulfate. Thereafter, the solvent is removed from the thus dried layer by distillation under reduced pressure. The residue thus obtained is purified by a column chromatography [eluent:hexane], to obtain 15.9 g of a colorless, solid mixture of 4-fluoro-5-methyl-benzo[b]thiophene and 6-fluoro-5-methyl-benzo[b]thiophene.

(4) To a solution of 15.9 g of a mixture of 4-fluoro-5-methyl-benzo[b]thiophene and 6-fluoro-5-methyl-benzo[b]thiophene in 160 ml of carbon tetrachloride are added 17 g of N-bromosuccinimide and 0.31 g of 2,2'-azobisisobutylonitrile. The resulting mixture is refluxed for two hours. After cooling, insolubles are removed from the thus cooled mixture by filtration, and the filtrate obtained is concentrated under reduced pressure. The residue obtained is suspended in 75 ml of acetic acid and 75 ml of water, and 26.8 g of hexamethylenetetramine is added thereto, after which the resulting mixture is refluxed for two hours. After cooling, 150 ml of water and 200 ml of ethyl acetate are added to the thus cooled mixture, and the resulting organic layer is separated, washed successively with water, an aqueous saturated sodium carbonate solution and a saturated saline solution and then dried over anhydrous magnesium sulfate. Thereafter, the solvent is removed from the thus dried layer by distillation under reduced pressure. The residue thus obtained is purified by a moderate pressure column chromatography [eluent:hexane:ethyl acetate=15:1], to obtain 1.71 g of 4-fluorobenzo[b]thiophene-5-carbaldehyde and 5.82 g of 6-fluorobenzo[b]thiophene-5-carbaldehyde.

Physical properties of each of the compounds are as follows:

4-Fluorobenzo [b]thiophene-5-carbaldehyde

IR (KBr) cm$^{-1}$: 1681; NMR (CDCl$_3$) δ value: 7.5–8.1 (4H, m), 10.55 (1H, s).

6-Fluorobenzo[b]thiophene-5-carbaldehyde

IR (KBr) cm$^{-1}$: 1684; NMR (CDCl$_3$) δ value: 7.3–7.6 (2H, m), 7.67 (1H, d, J=10.3 Hz), 8.34 (1H, d, J=6.4 Hz), 10.46 (1H, s).

In the same manner, the following compounds are obtained:

7-Fluorobenzo[b]thiophene-5-carbaldehyde

IR (KBr) cm$^{-1}$: 1678; NMR (CDCl$_3$) δ value: 7.2–7.8 (3H, m), 8.16 (1H, s), 10.60 (1H, s).

4-Bromobenzo[b]thiophene-5-carbaldehyde

IR (KBr) cm$^{-1}$: 1674; NMR (CDCl$_3$) δ value: 7.1–8.0 (4H, m), 10.54 (1H, s).

6-Bromobenzo[b]thiophene-5-carbaldehyde

IR (KBr) cm$^{-1}$: 1681; NMR (CDCl$_3$) δ value: 7.3–7.6 (2H, m), 8.18 (1H, s), 8.41 (1H, s), 10.51 (1H, s).

4-Chlorobenzo[b]thiophene-5-carbaldehyde

IR (KBr) cm$^{-1}$: 1678; NMR (CDCl$_3$) δ value: 7.3–8.2 (4H, m), 10.66 (1H, s).

6-Chlorobenzo[b]thiophene-5-carbaldehyde

IR (KBr) cm$^{-1}$: 1678; NMR (CDCl$_3$) δ value: 7.2–7.7 (2H, m), 7.98 (1H, s), 8.42 (1H, s), 10.60 (1H, s).

REFERENCE EXAMPLE 2

(1) In a solution of 5 g of benzo[b]thiophene-5-carbaldehyde in 100 ml of benzene are added 20 ml of ethylene glycol and a catalytic amount of p-toluene-sulfonic acid, and the resulting mixture is refluxed for two hours using an azeotropic dehydration apparatus. After cooling, 200 ml of water and 100 ml of ethyl acetate are added to the thus cooled mixture, and the resulting organic layer is separated, washed successively with water and a saturated saline solution and dried over anhydrous magnesium sulfate. Thereafter, the solvent is removed from the thus dried layer by distillation under reduced pressure. The residue obtained is purified by a moderate pressure column chromatography [eluent:hexane:ethyl acetate=10:1], to obtain 6.12 g of colorless, solid 5-(1,3-dioxoran-2-yl)benzo[b]thiophene.

NMR (CDCl$_3$) δ value: 3.9–4.3 (4H, m), 5.94 (1H, s), 7.2–7.6 (3H, m), 7.7–8.1 (2H, m)

(2) A solution of 1.5 g of 5-(1,3-dioxoran-2-yl)benzo[b] thiophene in 15 ml of tetrahydrofuran is cooled to −40° C., at which temperature 4.55 ml of 1.6 M hexane solution of n-butyllithium is then dropwise added to the solution. The temperature of the resulting reaction mixture is elevated to −10° C., and then lowered to −40° C. again, at which 0.45 ml of methyl iodide is added to the thus re-cooled reaction mixture. The temperature of the resulting mixture is elevated to room temperature. 30 Milliliters of water and 30 ml of ethyl acetate are added thereto, and the resulting organic layer is separated, washed successively with water and a saturated saline solution and dried over anhydrous magnesium sulfate. Thereafter, the solvent is removed from the thus dried layer by distillation under reduced pressure. The residue obtained is purified by a moderate pressure column chromatography [eluent:hexane:ethyl acetate=10:1], to obtain 1.45 g of colorless, solid 2-methyl-5-(1,3-dioxoran-2-yl)benzo[b]thiophene.

NMR (CDCl$_3$) δ value: 2.55 (3H, s), 3.9–4.3 (4H, m), 5.89 (1H, s), 6.9–8.0 (4H, m).

(3) A catalytic amount of p-toluenesulfonic acid is added to a solution of 1.5 g of 2-methyl-5-(1,3-dioxoran-2-yl)benzo [b]thiophene in 20 ml of acetone at room temperature, at which temperature the resulting mixture is stirred for 30 minutes. After the reaction, the solvent is removed from the reaction mixture by distillation under reduced pressure. The residue obtained are added 20 ml of water and 20 ml of ethyl acetate, after which the resulting organic layer is separated, washed successively with water and a saturated saline solution and then dried over anhydrous magnesium sulfate. The solvent is thereafter removed from the thus dried layer by distillation under reduced pressure, to obtain 1.15 g of colorless, solid 2-methylbenzo[b]thiophene-5-carbaldehyde.

IR (KBr) cm$^{-1}$: 1694; NMR (CDCl$_3$) δ value: 2.60 (3H, s), 5.89 (1H, s), 7.0–8.4 (4H, m), 10.10 (1H, s).

REFERENCE EXAMPLE 3

(1) To a solution of 3 g of benzo[b]thiophene-5-carbaldehyde in 30 ml of acetic acid is dropwise added 1.43 ml of bromine with ice-cooling. The temperature of the reaction mixture is elevated to room temperature, at which temperature the mixture is stirred for three hours. After the reaction, 50 ml of water and 50 ml of ethyl acetate are added to the thus stirred reaction mixture, and the resulting organic layer was separated, washed successively with water, a saturated aqueous sodium hydrogencarbonate solution and a saturated saline solution and then dried over anhydrous magnesium sulfate. Thereafter, the solvent is removed from the thus dried layer by distillation under reduced pressure. The residue obtained is purified by a moderate pressure column chromatography [eluent:hexane ethyl acetate=20:1], to obtain 4.2 g of 3-bromobenzo[b]thiophene-5-carbaldehyde.

NMR (CDCl$_3$) δ value: 7.5–8.4 (4H, m), 10.19 (1H, s).

(2) The same procedure as in Reference Example 2 (1) is repeated, except that 3-bromobenzo[b]thiophene-5-carbaldehyde is substituted for the benzo[b]thiophene-5-carbaldehyde, to obtain 3-bromo-5-(1,3-dioxoran-2-yl)-benzo[b]thiophene.

NMR (CDCl$_3$) δ value: 3.9–4.2 (4H, m), 5.93 (1H, s), 7.3–8.0 (4H, m).

(3) The same procedure as in Reference Example 2 (2) is repeated, except that 3-bromo-5-(1,3-dioxoran-2-yl)benzo [b]thiophene is substituted for the 5-(1,3-dioxoran-2-yl) benzo[b]thiophene and diethyl ether is substituted for the tetrahydrofuran, to obtain 3-methyl-benzo[b]thiophene-5-carbaldehyde.

NMR (CDCl$_3$) δ value: 2.51 (3H, s), 7.0–8.4 (4H, m), 10.15 (1H, s).

REFERENCE EXAMPLE 4

The same procedure as in Reference Example 2 (2) and Reference Example 2 (3) is repeated, except that N-fluorobenzenesulfonimide is substituted for the methyl iodide to obtain 2-fluorobenzo[b]thiophene-5-carbaldehyde from 5-(1,3-dioxoran-2-yl)benzo[b]thiophene.

NMR (CDCl$_3$) δ value: 6.84 (1H, d J=2.0 Hz), 7.6–8.4 (3H, m), 10.09 (1H, s).

REFERENCE EXAMPLE 5

The same procedure as in Reference Example 2 (2) and Reference Example 2 (3) is repeated, except that 3-bromo-5-(1,3-dioxoran-2-yl)benzo[b]thiophene is substituted for the 5-(1,3-dioxoran-2-yl)benzo[b]thiophene; diethyl ether is substituted for the tetrahydrofuran; and N-fluorobenzenesulfonimide is substituted for the methyl iodide, to obtain 3-fluorobenzo[b]thiophene-5-carbaldehyde from 3-bromo-5-(1,3-dioxoran-2-yl)benzo[b]thiophene.

NMR (CDCl$_3$) δ value: 6.99 (1H, d, J=2.0 Hz), 7.7–8.4 (3H, m), 10.14 (1H, s).

REFERENCE EXAMPLE 6

(1) To a solution of 2.0 g of 5-(1,3-dioxoran-2-yl)benzo[b] thiophene in 15 ml of tetrahydrofuran is added dropwise 6.06 ml of a 1.6 M hexane solution of n-butyllithium at −78° C. The temperature of the reaction mixture was elevated to −10° C. and thereafter lowered again to −78° C., after which 1.55 g of bromine is added to the thus re-cooled reaction mixture. The temperature of the resulting mixture is elevated to room temperature, and thereafter, 30 ml of water and 30 ml of ethyl acetate are added thereto. The resulting organic layer is separated, washed successively with water and a saturated saline solution, and then dried over anhydrous magnesium sulfate. Thereafter, the solvent is removed from the thus dried layer by distillation under reduced pressure. The residue obtained is purified by a moderate pressure column chromatography [elueant: toluene], to obtain 2.45 g of colorless, solid 2-bromo-5-(1,3-dioxoran-2-yl)benzo[b]thiophene.

NMR (CDCl$_3$) δ value: 3.9–4.3 (4H, m), 5.89 (1H, s), 7.2–8.0 (4H, m).

(2) To a solution of 2.5 g of 2-bromo-5-(1,3-dioxoran-2-yl) benzo[b]thiophene in 50 ml of toluene are added 6.44 g of phenyltri-n-butyltin and 0.05 g of tetrakis (triphenylphosphine)palladium (0), and the resulting mixture is refluxed under a nitrogen atmosphere for five hours. The reaction mixture is cooled to room temperature. Thereafter, 30 ml of water and 30 ml of ethyl acetate are added to the thus cooled reaction mixture. Thereafter, insolubles are removed from the resulting mixture by filtration. Thereafter, the resulting organic layer is separated, washed successively with water and a saturated saline solution and then dried over anhydrous magnesium sulfate. Thereafter, the solvent is removed from the thus dried layer by distillation under reduced pressure. The residue obtained is purified by a column chromatography [eluent:hexane:ethyl acetate=20:1], to obtain 1.20 g of colorless, solid 2-phenyl-5-(1,3-dioxoran-2-yl)benzo[b] thiophene.

(3) In the same manner as in Reference Example 2 (3), 2-phenylbenzo[b]thiophene-5-carbaldehyde is obtained from 2-phenyl-5-(1,3-dioxoran-2-yl)benzo[b]thiophene.

IR (KBr) cm$^{-1}$: 1692; NMR (CDCl$_3$) δ value: 7.2–8.4 (9H, m), 10.13 (1H, s).

In the same manner, the following compound is obtained:
3-Phenylbenzo[b]thiophene-5-carbaldehyde IR (KBr) cm$^{-1}$: 1686; NMR (CDCl$_3$) δ value: 7.3–8.1 (8H, m), 8.37 (1H, m), 10.09 (1H, s).

REFERENCE EXAMPLE 7

(1) The same procedure as in Reference Example 1 (1) and Reference Example 1 (2) is repeated, except that methyl 4-amino-2-methylbenzoate is substituted for the 3-fluoro-4-methylaniline, to obtain methyl 4-(2,2-diethoxyethylthio)-2-methylbenzoate.

NMR (CDCl$_3$) δ value: 1.20 (6H, t, J=7.0 Hz), 2.57 (3H, s), 3.18 (2H, d, J=5.4 Hz), 3.3–3.8 (4H, m), 3.86 (3H, s), 4.67 (1H, t, J=5.4 Hz), 7.0–7.3 (2H, m), 7.7–7.9 (1H, m).

(2) The same procedure as in Reference Example 1 (3) is repeated, except that methyl 4-(2,2-diethoxyethylthio)-2-methylbenzoate is substituted for the 1,1-diethoxy-2-(3-fluoro-4-methylphenylthio)ethane, to obtain a mixture of methyl 4-methylbenzo[b]thiophene-5-carboxylate and methyl 6-methylbenzo[b]thiophene-5-carboxylate.

(3) In 20 ml of tetrahydrofuran is suspended 0.37 g of lithium aluminum hydride. Thereafter, a solution of 2 g of a mixture of methyl 4-methylbenzo[b]thiophene-5-carboxylate and methyl 6-methylbenzo[b]thiophene-5-carboxylate in 20 ml of tetrahydrofuran is dropwise added to the suspension. The temperature of the resulting suspension is elevated to room temperature, and 30 ml of water and 30 ml of ethyl acetate are added thereto, and the resulting mixture is filtered. The resulting organic layer is separated, washed successively with water and a saturated saline solution and then dried over anhydrous magnesium sulfate. The solvent is removed from the thus dried layer by distillation under reduced pressure. The residue obtained is purified by a column chromatography [eluent:hexane:ethyl acetate=10:1], to obtain 1.7 g of a mixture of 4-methylbenzo [b]thiophene-5-methanol and 6-methylbenzo[b]thiophene-5-methanol as colorless solid.

(4) In 17 ml of chloroform is dissolved 1.7 g of a mixture of 4-methylbenzo[b]thiophene-5-methanol and 6-methylbenzo [b]thiophene-5-methanol, and 4.1 g of manganese dioxide is added thereto at room temperature. Thereafter, the resulting mixture is refluxed for one hour. After the reaction, insolubles are removed from the resulting reaction mixture by filtration and the filtrate obtained is concentrated under reduced pressure. The residue obtained is purified by a moderate pressure column chromatography [eluent:hexane:toluene=1:1], to obtain 0.65 g of 4-methylbenzo[b]thiophene-5-carbaldehyde as colorless solid and 0.48 g of 6-methyl-benzo[b]thiophene-5-carbaldehyde as colorless solid.

Physical properties of each of the compounds are as follows:
4-Methylbenzo[b]thiophene-5-carbaldehyde IR (KBr) cm$^{-1}$: 1673; NMR (CDCl$_3$) δ value: 2.95 (3H, s), 7.5–7.9 (4H, m), 10.50 (1H, s).
6-Methylbenzo[b]thiophene-5-carbaldehyde IR (KBr) cm$^{-1}$: 1696; NMR (CDCl$_3$) δ value: 2.77 (3H, s), 7.2–7.6 (2H, m), 7.75 (1H, s), 8.26 (1H, s), 10.35 (1H, s).

REFERENCE EXAMPLE 8

In the same manner as in Reference Example 6, 6-methoxybenzo[b]thiophene-5-carbaldehyde is obtained from 4-amino-2-methoxybenzoic acid.

NMR (CDCl$_3$) δ value: 3.99 (3H, s), 7.33 (2H, m), 7.42 (1H, s), 8.28 (1H, s), 10.56 (1H, s).

REFERENCE EXAMPLE 9

(1) To a solution of 2.04 g of diisopropylamine in 30 ml of tetrahydrofuran is dropwise added 9.19 ml of 1.6 M n-hexane solution of n-butyllithium at −20°C. At the same temperature, the resulting mixture is stirred for one hour and then cooled to −70° C., at which temperature a solution of 3 g of 3,5-difluorobromobenzene in 10 ml of tetrahydrofuran is dropwise added thereto over 30 minutes. The temperature of the resulting reaction mixture is elevated to −40° C. and then lowered again to −70° C., at which temperature 0.97 ml of methyl iodide is then added thereto. The temperature of the resulting mixture is elevated to room temperature, and 80 ml of water and 80 ml of ethyl acetate are then added thereto, after which the resulting organic layer is separated, washed successively with water and a saturated saline solution and then dried over anhydrous magnesium sulfate. Thereafter, the solvent is removed from the thus dried layer by distillation under reduced pressure. The residue obtained is purified by a column chromatography [eluent:hexane:ethyl acetate=10:1], to obtain 1.98 g of colorless, oily 4-bromo-2,6-difluorotoluene.

NMR (CDCl$_3$) δ value: 2.23 (3H, t, J=1.5 Hz), 7.00 (2H, d, J=6.3 Hz).

(2) To a solution of 1.98 g of 4-bromo-2,6-difluorotoluene in 20 ml of tetrahydrofuran is dropwise added 5.7 ml of 1.6 M n-hexane solution of n-butyllithium at −70° C. The resulting mixture is then stirred at the same temperature for one hour. Then, a solution of 2.88 g of 2,2,2',2'-tetraethoxydiethyl disulfide in 5 ml of tetrahydrofuran is dropwise added to the thus stirred reaction mixture at the same temperature. The temperature of the resulting mixture is elevated to room temperature and 80 ml of water and 80 ml of ethyl acetate are added thereto. The resulting organic layer is separated, washed successively with water and a saturated saline solution and then dried over anhydrous magnesium sulfate. Thereafter, the solvent is removed from the thus dried layer by distillation under reduced pressure. The residue obtained is purified by a column chromatography

[eluent:hexane:ethyl acetate=20:1], to obtain 2.1 g of colorless, oily 1,1-diethoxy-2-(3,5-difluoro-4-methylphenylthio)ethane.

NMR (CDCl$_3$) δ value: 1.20 (3H, t, J=7.0 Hz), 1.23 (3H, t, J=7.2 Hz), 2.1 (3H, t, J=1.7 Hz), 3.10 (2H, d, J=5.6 Hz), 3.4–3.9 (4H, m), 4.64 (1H, t, J=5.6 Hz), 6.87 (2H, d, J=7.6 Hz).

(3) The same procedure as in Reference Example 1 (3) is repeated, except that 1,1-diethoxy-2-(3,5-difluoro-4-methylphenylthio)ethane is substituted for the 1,1-diethoxy-2-(3-fluoro-4-methylphenylthio)ethane, to obtain 4,6-difluoro-5-methylbenzo[b]thiophene.

NMR (CDCl$_3$) δ value: 2.31 (3H, t, J=1.9 Hz), 7.2–7.5 (3H, m).

(4) To a solution of 0.48 g of 4,6-difluoro-5-methylbenzo[b]thiophene in 5 ml of carbon tetrachloride are added 0.92 a of N-bromosuccinimide and 0.01 g of 2,2'-azobisisobutylonitrile, and the resulting mixture is refluxed for 16 hours. After cooling, insolubles are removed from the thus cooled mixture by filtration, and the filtrate obtained is concentrated under reduced pressure. The residue obtained is purified by a column chromatography [eluent:hexane], to obtain 0.18 g of colorless, solid 5-bromomethyl-4,6-difluorobenzo[b]thiophene.

NMR (CDCl$_3$) δ value: 4.67 (2H, t, J=1.2 Hz), 7.2–7.5 (3H, m).

(5) To a solution of 0.18 g of 5-bromomethyl-4,6-difluorobenzofb]thiophene in 5 ml of N,N-dimethylformamide is added 0.23 g of potassium acetate, and the resulting mixture is stirred at 60° C. for one hour. The temperature of the thus stirred mixture is lowered to room temperature, and 10 ml of water and 10 ml of ethyl acetate are added thereto. Thereafter, the resulting organic layer is separated, washed successively with water and a saturated saline solution and then dried over anhydrous magnesium sulfate. Thereafter, the solvent is removed from the thus dried layer by distillation under reduced pressure, to obtain 0.14 g of colorless, oily 5-acetoxymethyl-4,6-difluorobenzo[b]thiophene.

NMR (CDCl$_3$) δ value: 2.07 (3H, s), 5.31 (2H, t, J=1.2 Hz), 7.3–7.6 (3H, m).

(6) To a solution of 0.14 g of 5-acetoxymethyl-4,6-difluorobenzo[b]thiophene in 5 ml of methanol is added 0.03 g of potassium hydroxide at room temperature, and thereafter, the resulting mixture is stirred at the same temperature for 30 minutes. After the reaction, 10 ml of water and 10 ml of ethyl acetate are added to the thus stirred reaction mixture. The resulting organic layer is separated, washed successively with water and a saturated saline solution, and then dried over anhydrous magnesium sulfate. Thereafter, the solvent is removed from the thus dried layer by distillation under reduced pressure to obtain 0.12 g of colorless, oily 5-hydroxymethyl-4,6-difluorobenzo[b]thiophene.

NMR (CDCl$_3$) δ value: 4.88 (2H, bs), 7.2–7.6 (3H, m).

(7) To a solution of 0.22 ml of oxalyl chloride in 10 ml of methylene chloride is added 0.35 ml of dimethyl sulfoxide at −78° C. Then, to the resulting solution is added dropwise a solution of 0.20 g of 5-hydroxymethyl-4,6-difluorobenzo[b]thiophene in 3 ml of methylene chloride. At the same temperature, the resulting mixture is stirred for one hour, and then, 0.70 ml of triethylamine is added thereto. The temperature of the resulting mixture is elevated to room temperature, and thereafter, 10 ml of water and 10 ml of ethyl acetate are added thereto, after which the resulting organic layer is separated, washed successively with water and a saturated saline solution and then dried over anhydrous magnesium sulfate. Then, the solvent is removed from the thus dried layer by distillation under reduced pressure. The residue obtained is purified by a column chromatography [eluent:hexane], to obtain 0.20 g of colorless, solid 4,6-difluorobenzo[b]thiophene-5-carbaldehyde.

IR (KBr) cm$^{-1}$: 1696; NMR (CDCl$_3$) δ value: 7.4–7.6 (3H, m), 10.49 (1H, s).

PRODUCTION EXAMPLE 1

(1) To a solution of 1.6 g of 6-fluorobenzo[b]thiophene-5-carbaldehyde in 30 ml of tetrahydrofuran is dropwise added 10 ml of 1.6 M tetrahydrofuran solution of 2-chloroethoxymethylmagnesium chloride at −30° C. over ten minutes, and thereafter, the resulting mixture is stirred while ice-cooling for one hour. Subsequently, the thus stirred reaction mixture is introduced into a mixture of 50 ml of ice water, 50 ml of ethyl acetate and 2 g of ammonium chloride, and the resulting mixture is adjusted to pH 2 with 6 N hydrochloric acid. Thereafter, the thus pH-adjusted mixture is stirred at the same temperature for five minutes. Subsequently, the thus stirred reaction mixture is adjusted to pH 6 with a saturated aqueous sodium hydrogencarbonate solution. Thereafter, the resulting organic layer is separated, washed successively with water and a saturated saline solution, and then dried over anhydrous magnesium sulfate. The solvent is then removed from the thus dried layer by distillation under reduced pressure. The residue obtained is purified by a column chromatography [eluent:toluene:ethyl acetate=4:1], to obtain 1.3 g of oily 2-(2-chloroethoxy)-1-(6-fluorobenzo[b]thiophen-5-yl)ethanol.

(2) A mixture of 0.61 g of 2-(2-chloroethoxy)-1-(6-fluorobenzo[b]thiophen-5-yl)ethanol, 3 ml of 50% aqueous diethylamine solution, 0.45 mg of potassium iodide and 20 ml of ethanol is refluxed for three hours. Subsequently, 3 ml of 50% aqueous diethylamine solution is added to the thus refluxed reaction mixture, and the resulting reaction mixture is further refluxed for three hours. The solvent is removed from the thus refluxed mixture by distillation under reduced pressure. To the residue obtained are added 30 ml of ethyl acetate and 30 ml of water, after which the resulting mixture is adjusted to pH 1.5 with 6 N hydrochloric acid. Thereafter, the aqueous layer is separated and washed with 10 ml of ethyl acetate. 30 Milliliters of ethyl acetate is then added to the thus washed layer, after which the resulting mixture, is adjusted to pH 10.5 with potassium carbonate. The organic layer is separated again, washed successively with 10 ml of water and 10 ml of a saturated saline solution, and then dried over anhydrous magnesium sulfate. The solvent is then removed from the thus dried layer by distillation under reduced pressure. The residue obtained is dissolved in 6 ml of ethanol. To the resulting solution are added 0.6 ml of 5 N dried hydrochloric acid-ethanol solution and 6 ml of diethyl ether. The mixture thus obtained is stirred at room temperature for one hour. The crystals precipitated are collected by filtration and washed with 2 ml of a liquid mixture of diethyl ether and ethanol (1:1) and then dried, to obtain 0.28 g of 2-[2-(N,N-diethylamino)ethoxy]-1-(6-fluorobenzo[b]thiophen-5-yl)ethanol hydrochloride.

Melting point: 125–126° C.; NMR (DMSO-d$_6$) δ value: 1.18 (6H, t, J=7.3 Hz), 2.9–4.0 (10 H, m), 5.0–5.4 (1H, m), 5.6–5.8 (1H, m), 7.4–8.2 (4H, m).

In the same manner, the following compounds are obtained:

2-[2-(N,N-Diethylamino)ethoxy]-1-(4-fluorobenzo[b]thiophen-5-yl)ethanol hydrochloride Melting point: 127–128° C.; NMR (DMSO-d$_6$) δ value: 1.18 (6H, t, J=7.3 Hz), 2.9–4.1 (10H, m), 5.1–5.4 (1H, m), 5.6–5.8 (1H, m), 7.4–8.0 (4H, m).

2-[2-(N,N-Diethylamino)ethoxy]-1-(7-fluorobenzo[b]
thiophen-5-yl)ethanol hydrochloride Melting point: 119–120° C.; NMR (DMSO-$d_6$) δ value:
1.15 (6H, t, J=7.3 Hz), 2.8–4.0 (10H, m), 4.7–5.1 (1H, m),
5.6–5.9 (1H, m), 7.1–8.0 (4H, m).

2-[2-(N,N-Diethylamino)ethoxy]-1-(2-fluorobenzo[b]
thiophen-5-yl)ethanol hydrochloride Melting point: 130–131° C.; NMR (DMSO-$d_6$) δ value:
1.17 (6H, t, J=7.3 Hz), 2.8–4.0 (10H, m), 4.86 (1H, m),
5.6–5.9 (1H, m), 7.1–8.0 (4H, m).

2-[2-(N,N-Diethylamino)ethoxy]-1-(3-fluorobenzo[b]
thiophen-5-yl)ethanol hydrochloride Melting point: 106–107° C.; NMR (DMSO-$d_6$) δ value:
1.17 (6H, t, J=7.3 Hz), 2.8–4.0 (10H, m), 4.8–5.2 (1H, m),
5.4–6.0 (1H, m), 7.4–8.2 (4H, m).

2-[2-(N,N-Diethylamino)ethoxy]-1-(2-methylbenzo[b]
thiophen-5-yl)ethanol hydrochloride Melting point: 136–137° C.; NMR (DMSO-$d_6$) δ value:
1.18 (6H, t, J=7.3 Hz), 2.54 (3H, s), 2.8–4.0 (10H, m),
4.7–5.0 (1H, m), 5.3–5.8 (1H, m), 7.0–8.0 (4H, m).

2-[2-(N,N-Diethylamino)ethoxy]-1-(3-methylbenzo[b]
thiophen-5-yl)ethanol 1/2 fumarate Melting point: 137–138° C.; NMR (DMSO-$d_6$) δ value:
0.99 (6H, t, J=7.3 Hz), 2.3–3.1 (9H, m), 3.4–3.8 (4H, m),
4.2–5.1 (3H, m), 6.53 (1H, s), 7.2–8.0 (4H, m).

2-[2-(N,N-Diethylamino)ethoxy]-1-(4-methylbenzo[b]
thiophen-5-yl)ethanol hydrochloride Melting point: 189–190° C.; NMR (DMSO-$d_6$) δ value:
1.17 (6H, t, J=7.2 Hz), 2.57 (3H, s), 2.8–4.0 (10H, m),
4.9–5.3 (1H, m), 5.4–5.7 (1H, m), 7.2–8.0 (4H, m).

2-[2-(N,N-Diethylamino)ethoxy]-1-(6-methylbenzo[b]
thiophen-5-yl)ethanol hydrochloride Melting point: 144–145° C.; NMR (DMSO-$d_6$) δ value:
1.17 (6H, t, J=7.2 Hz), 2.41 (3H, s), 2.7–4.1 (10H, m),
4.8–5.3 (1H, m), 5.4–5.8 (1H, m), 7.2–8.1 (4H, m).

1-(4-Chlorobenzo[b]thiophen-5-yl)-2-[2-(N,N-dimethylamino)ethoxy]ethanol hydrochloride Melting point: 148–149° C.; NMR (DMSO-$d_6$) δ value:
1.17 (6H, t, J=7.2 Hz), 2.8–4.1 (10H, m), 5.1–5.4 (1H, m),
5.7–6.0 (1H, m), 7.3–8.2 (4H, m).

1-(6-Chlorobenzo[b]thiophen-5-yl)-2-[2-(N,N-diethylamino)ethoxy]ethanol hydrochloride Melting point: 140–141° C.; NMR (DMSO-$d_6$) δ value:
1.17 (6H, t, J=7.2 Hz), 2.6–4.1 (10H, m), 5.0–5.4 (1H, m),
5.7–6.1 (1H, m), 7.3–8.2 (4H, m).

2-[2-(N,N-Diethylamino)ethoxy]-1-(2-phenylbenzo[b]
thiophen-5-yl)ethanol hydrochloride Melting point: 131–135° C.; NMR (DMSO-$d_6$) δ value:
1.18 (6H, t, J=7.1 Hz), 2.8–4.2 (10H, m), 4.7–5.1 (1H, m),
7.2–8.1 (9H, m).

2-[2-(N,N-Diethylamino)ethoxy]-1-(3-phenylbenzo[b]
thiophen-5-yl)ethanol hydrochloride Melting point: 158–160° C.; NMR (DMSO-$d_6$) δ value:
1.14 (6H, t, J=7.2 Hz), 2.8–4.2 (10H, m), 4.7–5.1 (1H, m),
7.2–8.2 (9H, m).

2-[2-(N,N-Diethylamino)ethoxy]-1-(6-methoxybenzo[b]
thiophen-5-yl)ethanol hydrochloride Melting point: 161–162° C.; NMR (DMSO-$d_6$), δ value:
1.19 (6H, t, J=7.3 Hz), 2.8–4.2 (10H, m), 3.87 (3H, s),
5.1–5.3 (1H, m), 7.2–7.6 (3H, m), 7.92 (1H, s), 1-(4,6-Difluorobenzo[b]thiophen-5-yl)-2-[2-(N,N-diethylamino)ethoxy]ethanol 1/2 fumarate Melting point: 135–136° C.; NMR (DMSO-$d_6$) δ value:
0.92 (6H, t, J=7.0 Hz), 2.4–2.9 (6H, m), 3.4–3.9 (4H, m),
5.1–5.5 (3H, m), 6.50 (1H, s), 7.4–7.9 (3H, m).

1-(4-Bromobenzo[b]thiophen-5-yl)-2-[2-(N,N-dimethylamino)ethoxy]ethanol hydrochloride Melting point: 150–151° C.; NMR (CDCl$_3$) δ value: 1.35
(6H, t, J=7.5 Hz), 2.8–4.2 (10H, m), 5.2–5.6 (2H, m),
7.3–7.4 (4H, m), 1-(6-Bromobenzo[b]thiophen-5-yl)-2-[2-( N,N-diethylamino)ethoxy]ethanol hydrochloride Melting point: 153–154° C.; NMR (CDCl$_3$) δ value: 1.41
(6H, t, J=7.5 Hz), 2.6–4.2 (10H, m), 5.3–5.6 (2H, m),
7.2–7.5 (2H, m), 7.99 (1H, s), 8.17 (1H, s).

2-[2-(N,N-Di-n-propylamino)ethoxy]-1-(6-fluorobenzo[b]
thiophen-5-yl)ethanol

Melting point: 143–144° C.; NMR (CDCl$_3$) δ value: 0.95
(6H, t, J=7.0 Hz), 1.4–2.2 (4H, m), 2.8–3.4 (6H, m), 3.5–4.2
(4H, m), 5.1–5.5 (2H, m), 7.1–7.6 (3H, m), 8.0–8.2 (1H, s).

1-(6-Fluorobenzo[b]thiophen-5-yl)-2-(1-piperazinyl)
ethanol

Melting point: 172–174° C. NMR (CDCl$_3$) δ value:
1.4–2.4 (6H, m), 2.6–4.2 (11H, m), 5.2–5.4 (1H, m), 7.1–7.6
(3H, m), 7.9–8.2 (1H, m).

1-(6-Fluorobenzo[b]thiophen-5-yl)-2-(1-morpholinyl)
ethanol

Melting point: 198–200° C.; NMR (DMSO-$d_6$) δ value:
2.6–4.8 (15H, m), 4.9–5.3 (1H, m), 7.4–8.2 (4H, m).

PRODUCTION EXAMPLE 2

(1) To a solution of 8.73 ml of oxalyl chloride in 90 ml of
methylene chloride is dropwise added 14.2 ml of dimethyl
sulfoxide at −70° C. over 30 minutes. The solution is stirred
at the same temperature for ten minutes, after which a
solution of 11 g of 2-(2-chloroethoxy)-1-(6-fluorobenzo[b]
thiophen-5-yl)ethanol in 90 ml of methylene chloride is
dropwise added thereto at the same temperature over 30
minutes. The resulting mixture is stirred at the same temperature for 30 minutes, and then, 50.2 ml of triethylamine
is dropwise added thereto. The temperature of the resulting
mixture is elevated to room temperature, and thereafter, 200
ml of diethyl ether is added thereto. Then, insolubles are
removed from the diethyl ether-added mixture by filtration.
Then, the solvent is removed from the resulting filtrate by
distillation under reduced pressure. To the residue obtained
are added 200 ml of water and 200 ml of ethyl acetate, and
then, the pH is adjusted to 1 with 1 N hydrochloric acid.
Thereafter, the resulting organic layer is separated, washed
successively with water and a saturated saline solution and
then dried over anhydrous magnesium sulfate. The solvent is
removed from the thus dried layer by distillation under
reduced pressure. To the residue obtained is added 50 ml of
diethyl ether, after which insolubles are collected by
filtration, to obtain 9.5 g of colorless, solid 2-(2-chloroethoxy)-1-(6-fluorobenzo[b]thiophen-5-yl)ethanone.

(2) To a solution of 4.5 g of 2-(2-chloroethoxy)-1-(6-fluorobenzo[b]thiophen-5-yl)ethanone in 45 ml of tetrahydrofuran is added 0.46 g of (R)-5,5-diphenyl-2-methyl-3,4-propano-1,3,2-oxazaborolidine at −10° C., and thereafter,
9.9 ml of 1 M borane solution of tetrahydrofuran is dropwise
added thereto. The temperature of the resulting mixture is
elevated to room temperature, and the mixture is stirred at
the same temperature for 1.5 hours, after which 100 ml of
water and 100 ml of ethyl acetate are added thereto. The
resulting organic layer is separated, washed successively
with water and a saturated saline solution and then dried
over anhydrous magnesium sulfate. The solvent is then
removed from the thus dried layer by distillation under
reduced pressure. The residue obtained is purified by a
column chromatography [eluent:toluene:ethyl acetate=
10:1], to obtain 4.5 g of oily (+)-2-(2-chloroethoxy)-1-(6-fluorobenzo[b]thiophen-5-yl)ethanol.

(3) In the same manner as in Production Example 1 (2),
(+)-1-(6-fluorobenzo[b]thiophen-5-yl)-2-[2-(N,N- diethylamino)ethoxy]ethanol hydrochloride is obtained from (+)-2-(2-chloroethoxy)-1-(6-fluorobenzo[b]thiophen-5-yl)ethanol.

Melting point: 138–139° C.; $[\alpha]_D$+40.8 (C=1.40, CH$_3$OH).

In the same manner, the following compound is obtained:

(−)-1-(6-Fluorobenzo[b]thiophen-5-yl)-2-[2-(N,N-diethylamino)ethoxy]ethanol hydrochloride Melting point: 138–139° C.; $[\alpha]_D$−40.3 (C=1.13, CH$_3$OH).

An explanation is made below of the NGF activity-potentiating effect of the 1,2-ethanediol derivative represented by the general formula [I] or its salt.

[Nervous process-elongating activity]

Test Compound

As test compounds, there are used the compounds disclosed in JP-A-3-47,158; JP-A-3-232,830 and JP-A-4-95,070 and the compounds obtained in Production Examples 1 and 2 which are shown in Tables 1 to 6. The melting points of the compounds other than those obtained in Production Examples 1 and 2 are also shown in Table 7. Incidentally, the compounds were dissolved in water or dimethyl sulfoxide.

TABLE 1

| No. | Compound |
|---|---|
| 1 | [structure] |
| 2 | [structure] |
| 3 | [structure] |
| 4 | [structure] |
| 5 | [structure] |

TABLE 1-continued

| No. | Compound |
|---|---|
| 6 | [structure] |

TABLE 2

| No. | Compound |
|---|---|
| 7 | [structure] |
| 8 | [structure] |
| 9 | [structure] |
| 10 | [structure] |
| 11 | [structure] |
| 12 | [structure] |

TABLE 3

| No. | Compound |
|---|---|
| 13 | [structure] |

TABLE 3-continued

| No. | Compound |
|---|---|
| 14 | 1-(benzo[b]thiophen-5-yl)-2-[(1-ethylpyrrolidin-3-yl)oxy]ethanol·HCl |
| 15 | 1-(benzofuran-5-yl)-2-[2-(dimethylamino)ethoxy]ethanol·HCl |
| 16 | 1-(benzofuran-5-yl)-2-(2-aminoethoxy)ethanol·½ fumarate |
| 17 | 1-(benzo[b]thiophen-5-yl)-2-[2-(diethylamino)ethoxy]ethanol·HCl |
| 18 | 1-(benzofuran-5-yl)-2-[2-(4-benzylpiperazin-1-yl)ethoxy]ethanol·2HCl |

TABLE 4

| No. | Compound |
|---|---|
| 19 | 1-(naphthalen-1-yl)-2-[2-(diethylamino)ethoxy]ethanol·HCl |
| 20 | 1-phenyl-2-[2-(dimethylamino)ethoxy]ethanol·HCl |
| 21 | 1-(3-methylphenyl)-2-[2-(dimethylamino)ethoxy]ethanol·HCl |

TABLE 4-continued

| No. | Compound |
|---|---|
| 22 | 1-(3-fluorophenyl)-2-[2-(dimethylamino)ethoxy]ethanol·HCl |
| 23 | 1-(2'-methylbiphenyl-4-yl)-2-[2-(dimethylamino)ethoxy]ethanol·HCl |
| 24 | 1-phenyl-2-{2-[(benzo[b]thiophen-5-ylmethyl)amino]ethoxy}ethanol·HCl |

TABLE 5

| No. | Compound |
|---|---|
| 25 | 1-(4-methylbenzo[b]thiophen-5-yl)-2-[2-(diethylamino)ethoxy]ethanol·HCl |
| 26 | 1-(4-chlorobenzo[b]thiophen-5-yl)-2-[2-(diethylamino)ethoxy]ethanol·HCl |
| 27 | 1-(3-phenylbenzo[b]thiophen-5-yl)-2-[2-(diethylamino)ethoxy]ethanol·HCl |
| 28 | 1-(6-methoxybenzo[b]thiophen-5-yl)-2-[2-(diethylamino)ethoxy]ethanol·HCl |
| 29 | (R)-1-(6-fluorobenzo[b]thiophen-5-yl)-2-[2-(diethylamino)ethoxy]ethanol·HCl |

TABLE 5-continued

| No. | Compound |
|---|---|
| 30 | 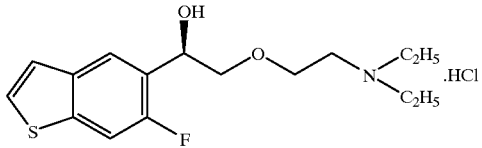 |

TABLE 6

| No. | Compound |
|---|---|
| 31 | ![structure 31] |
| 32 | ![structure 32] |
| 33 | ![structure 33] |
| 34 | ![structure 34] |
| 35 | ![structure 35] |
| 36 | ![structure 36] |

TABLE 6-continued

| No. | Compound |
|---|---|
| 37 | 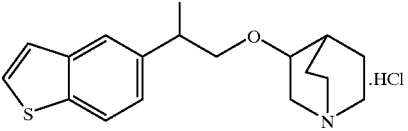 |

TABLE 7

| Compound No. | Melting point (° C.) |
|---|---|
| 1 | 120–120.5 |
| 2 | 119.5–120.5 |
| 3 | 191.5–192.5 |
| 4 | 180–180.5 |
| 5 | 134–137.5 |
| 6 | 143.5–145 |
| 9 | 207.5–210 |
| 10 | 166.5–167.5 |
| 11 | 232–234 |
| 12 | 191.5–193 |
| 13 | 199–202 |
| 14 | 163–169 |
| 15 | 168–169.5 |
| 16 | 170–173 |
| 17 | 109–110 |
| 18 | 234–234.5 |
| 19 | 155.5–157 |
| 20 | 184–185 |
| 21 | 165–166 |
| 22 | 171–172 |
| 23 | 223–225 |
| 24 | 157–161 |

TEST CELL

PC12 cell [rat adrenal medullary xanthoma (NGF-responding cell)]

TEST MEDIUM

RPMI 1640 (mtd. by Nissui pharmaceutical Co., Ltd.) supplemented with 10% heat-inactivated (56° C., 30 min.) horse serum (Summit Biotechnology Inc.), 5% heat-inactivated (56° C., 30 min.) fetal calf serum (mfd. by Gibco Inc.) and 60 μg/ml of Kanamycine sulfate is used.

TEST METHOD

PC12 cells are adjusted at a density of $8 \times 10^3$ cells/ml with the above culture medium and plated out into 6-well plate (mfd. by Falcon Inc.) in a portion of 2 ml/well. Subsequently, 2.5S-NGF (mfd. by Wako Inc.) dissolved in 0.1% bovine serum albumin/phosphate-buffered saline solution, is added at a final concentration of 100 ng/ml and the test compounds are added at final concentration of $10^{-5}$M at the same time. Cells are incubated at 37° C. in a humidified incubator with 5% $CO_2$ atmosphere. On the 5th day after the treatment of the test compounds, cells from three randomly chosen phase contrast microscope fields are counted. The proportion of cells bearing neutrites longer than cell body to the other cells is determined. Besides, the proportion of the control group free from the test compound is taken as 100%. The results are shown in Table 8.

TABLE 8

| Compound No. | Concentration of test compound added (M) | Nervous process elongation activity (%) |
|---|---|---|
| 1 | $10^{-5}$ | 136 |
| 2 | $10^{-5}$ | 129 |
| 3 | $10^{-5}$ | 123 |
| 4 | $10^{-5}$ | 117 |
| 5 | $10^{-5}$ | 121 |
| 6 | $10^{-5}$ | 113 |
| 7 | $10^{-5}$ | 125 |
| 8 | $10^{-5}$ | 130 |
| 9 | $10^{-5}$ | 123 |
| 10 | $10^{-5}$ | 131 |
| 11 | $10^{-5}$ | 112 |
| 12 | $10^{-5}$ | 124 |
| 13 | $10^{-5}$ | 118 |
| 14 | $10^{-5}$ | 126 |
| 15 | $10^{-5}$ | 116 |
| 16 | $10^{-5}$ | 123 |
| 17 | $10^{-5}$ | 113 |
| 18 | $10^{-5}$ | 121 |
| 19 | $10^{-5}$ | 112 |
| 20 | $10^{-5}$ | 124 |
| 21 | $10^{-5}$ | 114 |
| 22 | $10^{-5}$ | 112 |
| 23 | $10^{-5}$ | 112 |
| 24 | $10^{-5}$ | 110 |
| 25 | $10^{-5}$ | 111 |
| 26 | $10^{-5}$ | 112 |
| 27 | $10^{-6}$ | 125 |
| 28 | $10^{-5}$ | 127 |
| 29 | $10^{-5}$ | 116 |
| 30 | $10^{-5}$ | 124 |
| 31 | $10^{-5}$ | 111 |
| 32 | $10^{-5}$ | 112 |
| 33 | $10^{-6}$ | 111 |
| 34 | $10^{-5}$ | 116 |
| 35 | $10^{-5}$ | 110 |
| 36 | $10^{-5}$ | 124 |
| 37 | $10^{-5}$ | 117 |

BEST MODE FOR CARRYING OUT THE INVENTION PREPARATION EXAMPLE 1
(Tablet)

Tablets each containing 50 mg of 2-[2-(N,N-diethylamino)ethoxy]-1-[benzo[b]thiophen-5-yl)ethanol hydrochloride (Compound No. 1) are prepared by the following method using the following recipe:
Per One Tablet:

| | | |
|---|---|---|
| Compound No. 1 compound | 50 mg | |
| Milk sugar | 20 mg | |
| Kollidon CL (mfd. by BASF) | 15 mg | (1) |
| Corn starch | 30 mg | |
| Avicel (mfd. by Asahi Chemical) | 50 mg | |
| Polyvinylpyrrolidone K-90 | 5 mg | |
| Light silicic acid anhydride | 18 mg | (2) |
| Magnesium stearate | 2 mg | |
| Total | 175 mg | |

A mixture of the components (1) is kneaded with 8% aqueous solution of polyvinylpyrrolidone K-90, and dried at 60° C., and thereafter, mixed with the components (2), after which the resulting mixture is tableted into circular tablets each having a diameter of 8 mm and a weight of 175 mg.

PREPARATION EXAMPLE 2 (Capsule)

Capsules each containing 50 mg of 2-[2-2-(N,N-diethylamino)ethoxy]-1-[benzo[b]thiophen-5-yl)ethanol hydrochloride (Compound No. 1) are prepared by the following method using the following recipe:
Per One Capsule:

| | | |
|---|---|---|
| Compound No. 1 compound | 50 mg | |
| Milk sugar | 20 mg | (1) |
| Corn starch | 53 mg | |
| Kollidon CL (mfd. by BASF) | 2 mg | |
| Polyvinylpyrrolidone K-90 | 5 mg | |
| Avicel PH302 (mfd. by Asahi Chemical) | 18 mg | (2) |
| Magnesium stearate | 2 mg | |
| Total | 150 mg | |

A mixture of the components (1) is kneaded with 8% aqueous solution of polyvinylpyrrolidone K-90, and the resulting mixture is dried at 60° C. and then mixed with the components (2). No. 3 gelatine capsules are filled with the resulting mixture in a proportion of 150 mg per one capsule to obtain capsules.

UTILIZABILITY IN INDUSTRY

The 1,2-ethanediol derivative represented by the general formula [I] or its salt has a NGF activity-potentiating effect, and is useful as a remedy for various diseases caused by degeneration of central nervous system and peripheral nervous system such as senile dementia of Alzheimer type, Huntington's chorea, various neuropathies, Riley-Day syndrome, traumatic nerve injury, amyotrophic lateral sclerosis (ALS) and the like.

We claim:

1. A compound for remedying a disease caused by degeneration of central or peripheral nervous system, comprising a 1,2-ethanediol derivative represented by the following formula or its salt:

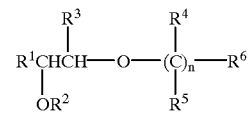

wherein $R^1$ represents a substituted or unsubstituted phenyl, naphthyl, indanyl, indenyl or tetrahydronaphthyl group; $R^2$ represents a hydrogen atom, a lower alkyl group or a hydroxyl-protecting group; $R^3$ represents a hydrogen atom or a lower alkyl group; $nR^4$'s may be the same as or different from one another and each represents a hydrogen atom or a lower alkyl group; $nR^5$'s may be the same as or different from one another and each represents a hydrogen atom or a lower alkyl group; $R^6$ represents a substituted or unsubstituted nitrogen-containing heterocyclic group; and n represents 0 or an integer of 1 to 6.

2. The compound of claim 1, wherein the disease is a member selected from the group consisting of senile dementia of Alzheimer type, Huntington's chorea, amyotrophic lateral sclerosis, neuropathies, Riley-Day syndrome and traumatic nerve injury.

3. A method of remedying a disease caused by degeneration of central or peripheral nervous system, comprising administering an effective amount of the 1,2-ethanediol derivative of claim 1 or a salt thereof to a patient in need thereof.

4. The method of claim 3, wherein the disease is a member selected from the group consisting of senile dementia of Alzheimer type, Huntington's chorea, amyotrophic lateral sclerosis, neuropathies, Riley-Day syndrome and traumatic nerve injury.

5. A pharmaceutical composition comprising a pharmaceutically effective amount of a 1,2-enthanediol derivative represented by the following formula or its salt:

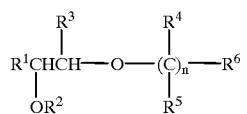

wherein $R^1$ represents a substituted or unsubstituted phenyl, naphthyl, indanyl, indenyl or tetrahydronaphthyl group; $R^2$ represents a hydrogen atom, a lower alkyl group or a hydroxyl-protecting group; $R^3$ represents a hydrogen atom or a lower alkyl group; $nR^4$'s may be the same as or different from one another and each represents a hydrogen atom or a lower alkyl group; $nR^5$'s may be the same as or different from one another and each represents a hydrogen atom or a lower alkyl group; $R^6$ represents a substituted or unsubstituted nitrogen-containing heterocyclic group; and n represents 0 or an integer of 1 to 6 and a pharmaceutically acceptable carrier or diluent.

* * * * *